(12) United States Patent
Stone

(10) Patent No.: US 6,666,848 B2
(45) Date of Patent: Dec. 23, 2003

(54) MEDICAL INJECTION APPARATUS

(75) Inventor: Corbett Stone, San Diego, CA (US)

(73) Assignee: Artes Medical USA, Inc., San Diego, CA (US)

( * ) Notice: Subject to any disclaimer, the term of this patent is extended or adjusted under 35 U.S.C. 154(b) by 0 days.

(21) Appl. No.: 10/172,773

(22) Filed: Jun. 14, 2002

(65) Prior Publication Data

US 2003/0018299 A1 Jan. 23, 2003

Related U.S. Application Data

(60) Provisional application No. 60/298,310, filed on Jun. 14, 2001, and provisional application No. 60/298,620, filed on Jun. 14, 2001.

(51) Int. Cl.[7] ............................................. A61M 51/78
(52) U.S. Cl. .................. 604/164.01; 604/239; 604/272; 604/135
(58) Field of Search ............................. 604/239, 272, 604/164.01, 135

(56) References Cited

U.S. PATENT DOCUMENTS

| | | | | |
|---|---|---|---|---|
| 2,603,782 A | * | 7/1952 | Spencer | 227/132 |
| 3,625,208 A | * | 12/1971 | Frost et al. | 604/68 |
| 3,782,380 A | * | 1/1974 | Van Der Gaast | 604/68 |
| 5,312,345 A | * | 5/1994 | Cole | 604/110 |
| 5,916,208 A | * | 6/1999 | Luther et al. | 604/508 |
| 6,203,533 B1 | * | 3/2001 | Ouchi | 604/264 |
| 6,500,157 B2 | * | 12/2002 | Luther | 604/264 |
| 6,508,802 B1 | * | 1/2003 | Rosengart et al. | 604/523 |
| 6,524,284 B1 | * | 2/2003 | Marshall | 604/272 |

* cited by examiner

Primary Examiner—Mark Bockelman
Assistant Examiner—Jeremy Thissell
(74) Attorney, Agent, or Firm—Stout, Uxa, Buyon & Mullins, LLP

(57) ABSTRACT

An injection apparatus includes components that facilitate injection of relatively viscous materials into a patient. An injection apparatus may include a transition-bore needle apparatus, which has a proximal end, a distal end, and a lumen extending from the proximal end to the distal end, in which the diameter of the proximal end is greater than the diameter of the distal end. An injection apparatus may include a hand-held injection facilitation apparatus, which may be coupled to a syringe. The hand-held injection facilitation apparatus can include a pivot arm and a body with a rod disposed within the body and coupled to the pivot arm. Movement of the pivot arm results in a proximal or distal movement of the rod within the body to effectively cause material to be expelled from the syringe. An injection apparatus may include a transition-bore needle apparatus and a hand-held injection facilitation apparatus in combination.

29 Claims, 8 Drawing Sheets

MEDICAL INJECTION APPARATUS

CROSS-REFERENCE TO RELATED APPLICATIONS

This application claims the benefit of U.S. Provisional Application No. 60/298,310, entitled INJECTION FACILITATION APPARATUS, and filed Jun. 14, 2001; and U.S. Provisional Application No. 60/298,620, entitled TRANSITION-BORE NEEDLE APPARATUS, and filed Jun. 14, 2001, the entire contents of which are hereby incorporated by reference.

BACKGROUND OF THE INVENTION

1. Field of the Invention

The present invention relates generally to medical devices and, more particularly, to injection apparatus that facilitate and improve the ability to pass viscous materials through lumens of small aperture.

2. Description of Related Art

The term "stress urinary incontinence" refers to a functionally insufficient urinary tract of a patient. In a patient having this condition, the tissue relaxation of the sphincter mechanism, located at the urinary outflow of the bladder into the urethra, can cause a loss of bladder control. Cystoscopes are typically used to study the urethra and bladder and to evaluate, for example, a patient's urinary incontinence condition. A typical cystoscope may comprise a tubular instrument equipped with, for example, a visual channel and a working channel, and constructed to be inserted through the urethra for viewing of the urethra and bladder.

Treatment of a urinary incontinence condition may comprise the injection of a filler material, such as collagen, into and adjacent to the urinary sphincter muscle at the bladder neck, to thereby bulk up the tissue and assist in the adequate closure of the urinary sphincter.

Acid reflux is a digestive disorder which similarly involves the tissue relaxation of a sphincter mechanism. In the case of acid reflux, which is commonly known as gastroesophageal reflux disease (GERD) or heartburn, the lower esophageal sphincter connecting the esophagus to the stomach begins to malfunction.

During proper operation of the lower esophageal sphincter, the lower esophageal sphincter opens to allow food to pass into the stomach and closes to prevent food and acidic stomach fluids from flowing back up into the esophagus. Gastroesophageal reflux occurs when the lower esophageal sphincter is weak or relaxes inappropriately, allowing the stomach's contents to retrograde or flow up into the esophagus.

This retrograde flow of gastric contents back into the esophagus, through what should be a one-way valve into the stomach, can damage the esophagus. More particularly, the contents of the stomach are very acidic; and the lining of the stomach is specially designed to cope with the lower pH contents. The esophagus, on the other hand, is not suited for such exposure to highly acidic materials. Thus, when acid retrogrades from the stomach into the esophageal tissues, irritation and inflammation will often result to these tissues.

The severity of tissue damage which can result from gastroesophageal reflux disease can depend on factors such as the dysfunctional level of the lower esophageal sphincter, the type and amount of fluid brought up from the stomach, and the neutralizing effect of the patient's saliva.

Another factor, which may affect the severity of a particular gastroesophageal reflux disorder, is the patient's esophageal motility. Lack of esophageal motility can occur through either of two mechanisms. When incomplete emptying of the esophagus into the stomach after ingestion of liquids or solids occurs, the motility of the esophagus can be said to be affected, resulting in esophageal reflux. Also, esophageal reflux can occur when small amounts of gastric contents, which may be refluxed into the lower esophagus, are not rapidly emptied back into the stomach. Delays in the emptying of this material, caused by an esophageal motility disorder, for example, can lead to irritation of the esophageal mucosa and possibly to the sensation of heartburn or the development of esophagitis.

Various tools and instruments have been used in the prior art for the treatment of urinary incontinence and acid reflux disease. Gastroscopes are typically used to study the esophagus and to evaluate, for example, a patient's acid reflux condition. A gastroscope typically comprises a flexible, lighted instrument that is inserted through the mouth and esophagus to view the stomach. Similarly, a cystoscope is typically inserted through a patient's urethra to facilitate evaluation of, for example, a urinary incontinence condition.

Treatment of either of the above-mentioned disorders may include one or more injections of a viscous material, such as collagen, into the vicinity of either the lower esophageal sphincter (for treating acid reflux) or the sphincter of the urethra (for treating urinary incontinence). These injection procedures typically involve elongate catheters for the delivery of viscous materials through the body passages and to the target sites of injection. The force required to deliver a viscous material through the delivery lumen of an elongate catheter will naturally increase as the length of the elongate catheter increases. Moreover, the types of elongate catheters used with these surgical procedures will typically have delivery lumens of relatively small cross-sectional areas, thus further augmenting the force required to deliver the viscous material through the length of the elongate catheter.

To compensate for the greater required force, it would be desirable to form the elongate catheter to have a lumen with a relatively large cross-sectional area to facilitate flow of the viscous material therethrough. Another design criterion is that the diameter of the needle tip should be relatively small to reduce tissue trauma at the injection site, to increase precision in some instances, and to reduce patient discomfort.

In order to meet the objectives of both a relatively large delivery lumen and a relatively small needle tip, a juncture must be formed at some point along the length of the needle to transition the needle diameter from a relatively large size to a relatively small size. If the transition point is abrupt or too great in magnitude, optimal flow of the viscous material through the needle may be inhibited.

SUMMARY OF THE INVENTION

An injection apparatus, as disclosed herein, may comprise a transition-bore needle apparatus to optimize the flow of viscous material from the injection apparatus. An injection apparatus, as disclosed herein, may comprise a hand-held injection facilitation apparatus which reduces the effort required to displace viscous material from the injection apparatus. The hand-held injection facilitation apparatus is structured to cooperatively interact with a syringe to cause displacement of viscous material from the syringe. An injection apparatus may comprise a combination of a transition-bore needle apparatus, and a hand-held injection facilitation apparatus, disclosed herein.

A transition-bore needle apparatus is provided to optimize the flow of a viscous material through a decreasing-diameter lumen of a needle. The transition-bore needle apparatus comprises a proximal end and a distal end, and the lumen extends from the proximal end of the transition-bore needle apparatus to the distal end of the transition-bore needle apparatus. A diameter at a proximal portion of the transition-bore needle apparatus is greater than a diameter at a distal portion of the transition-bore needle apparatus.

In accordance with one aspect of the present invention, the proximal portion of the transition-bore needle apparatus comprises a first needle having a first diameter, and the distal portion of the transition-bore needle apparatus comprises a second needle having a second diameter. The first diameter is greater than the second diameter. The first needle comprises a proximal end, a distal end, and a first lumen extending through the first needle from the proximal end to the distal end, and the second needle similarly comprises a proximal end, a distal end, and a second lumen extending through the second needle from the proximal end of the second needle to the distal end of the second needle.

The lumen of the transition-bore needle apparatus comprises both a portion of the first lumen of the first needle and a portion of the second lumen of the second needle. A juncture thus exists within the lumen of the transition-bore needle apparatus, where the diameter thereof transitions from the first diameter to the second diameter. At this juncture, the proximal end of the first needle terminates within the second lumen. In accordance with an aspect of the present invention, the proximal end of the first needle is beveled to improve a flow of viscous material through the lumen of the transition-bore needle apparatus. In accordance with another aspect of the present invention, the proximal end of the first needle is chamfered to improve a flow of viscous material through the lumen of the transition-bore needle apparatus. According to yet another aspect of the present invention, the proximal end of the first needle is both chamfered and beveled to improve a flow of viscous material through the lumen of the transition-bore needle apparatus.

The transition-bore needle apparatus of the facilitates the injection of viscous filler material by optimizing a flow of the viscous material through the lumen of the transition-bore needle apparatus. The transition-bore needle apparatus may be used in conjunction with surgical instruments, such as endoscopes, cystoscopes, and gastroscopes, to aid in intraluminal injections of materials into body tissues within body lumens. When the body lumen comprises an esophagus, the gastroscope is inserted through the esophagus into a vicinity of the lower esophageal sphincter, and a long needle is used to inject a filler material into and adjacent to the lower esophageal sphincter tissues for the treatment of acid reflux. When the body lumen comprises a female urethra, the cystoscope is inserted through the urethra to the urinary sphincter adjacent to the bladder neck, and a long needle is used to inject a filler material into and adjacent to the urinary sphincter tissues for the treatment of stress urinary incontinence. The filler material may also be injected, for example, along a greater length of the urethra.

The injection apparatus disclosed herein thus facilitates the injection of viscous filler materials, and may provide for increased speed, accuracy and efficiency in dispensing such materials. The injection of bulking agents into the respective tissues of body sphincters helps fortify the respective tissue structures and re-establish normal sphincter control. The transition-bore needle apparatus of the injection apparatus and associated methods of operation disclosed herein may be configured for and used on other body passages and tissues (e.g., wrinkles) as well in modified embodiments.

An injection apparatus may comprise a hand-held injection facilitation apparatus to increase the precision of dispensing of a material from a syringe. The injection facilitation apparatus may be used in conjunction with surgical instruments, such as endoscopes, cystoscopes, and gastroscopes, to aid in transurethral injection for intraluminal injections of materials into body tissues, and to visualize tissue within a body lumen. When the body lumen comprises an esophagus, the gastroscope is inserted through the esophagus into a vicinity of the lower esophageal sphincter, and a long needle is used to inject a filler material into and adjacent to the lower esophageal sphincter tissues for the treatment of acid reflux. When the body lumen comprises a female urethra, the gastro cystoscope is inserted through the urethra into the urinary sphincter adjacent to the bladder neck, and a long needle is used to inject a filler material into and adjacent to the urinary sphincter muscle tissues for the treatment of stress urinary incontinence. The filler material may also be injected, for example, along the entire length of the urethra.

The hand-held injection facilitation apparatus of the injection apparatus facilitates the injection of the viscous filler materials, and provides for increased accuracy in dispensing such materials. The injection of a urinary bulking agents into the respective tissues of body sphincters helps fortify the respective tissue structures and re-establish normal bladder sphincter control. The apparatus of the present invention and associated methods of operation disclosed herein may be configured for and used on other body passages as well in modified embodiments.

In accordance with one aspect of the present invention, an injection facilitation apparatus is constructed for use in conjunction with a stainless steel needle tip catheter that can be introduced into a patient's urethra or esophagus in a treatment for urinary incontinence or gastro-esophageal reflux. The treatment for gastro-esophageal reflux disease may be fashioned to increase the strength or the length of the lower esophageal sphincter (LES) by depositing a viscous material around the lower esophageal sphincter. The suspension can be injected via a syringe and needle directly into the specific areas where the viscous agent is desired. A principal use of the exemplary embodiment is to accurately dispense the viscous material to thereby alter the physiological architecture of the patient's sphincter and adjacent tissues. Thus the bio-mechanical characteristics of the sphincter and surrounding tissues are altered to alleviate urinary incontinence and gastro-esophageal reflux.

The subjects and objects of this disclosure relate to novel methods and instruments for facilitating the controlled dispensing of viscous material in the interior of the body, including but not limited to soft tissues, and lumen structures (e.g., esophagus, urethra).

The present invention, together with additional features and advantages thereof, may best be understood by reference to the following description taken in connection with the accompanying illustrative drawings.

BRIEF DESCRIPTION OF THE DRAWINGS

FIG. 5A is a side-elevational view of the housing of the injection facilitation apparatus of FIG. 5, taken along the line A—A of FIG. 5;

FIG. 5B is a side-elevational view of an internal end of the pivot arm of the injection facilitation apparatus of FIG. 5, taken along the line B—B of FIG. 5;

DETAILED DESCRIPTION OF THE PRESENTLY PREFERRED EMBODIMENTS

An injection apparatus that facilitates displacement of viscous materials from a catheter may comprise a transition-bore needle apparatus, a hand-held injection facilitation apparatus, or a combination thereof. The transition-bore needle apparatus and the hand-held injection facilitation apparatus, as disclosed herein, can reduce the effort required by a person to displace the viscous material from the injection apparatus. In general, the transition-bore needle apparatus can reduce the effort required to expel material from a catheter by graduating changes of the internal diameter of the lumens of catheters. The hand-held injection facilitation apparatus can reduce the effort required to expel material from a catheter by permitting a person to control the longitudinal displacement of a syringe plunger using a gripping action of the person's hand as compared to a digit action between the person's thumb and fingers, as is conventionally practiced.

Figure 1B:
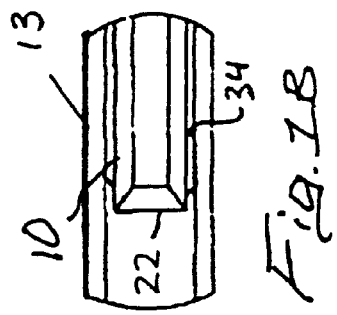
FIG. 1B is a cross-sectional view of a proximal end of a distal needle with edges chamfered at about a 45 degree angle from the longitudinal axis of the distal needle.
Figure 1A:
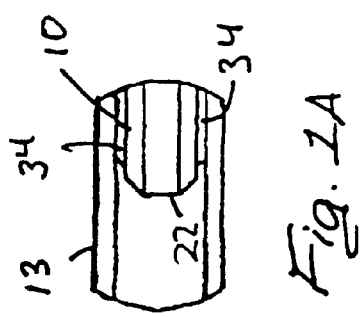
FIG. 1A is a cross-sectional view of a proximal end of a distal needle with edges beveled at about a 45 degree angle from the longitudinal axis of the distal needle.
Figure 1:
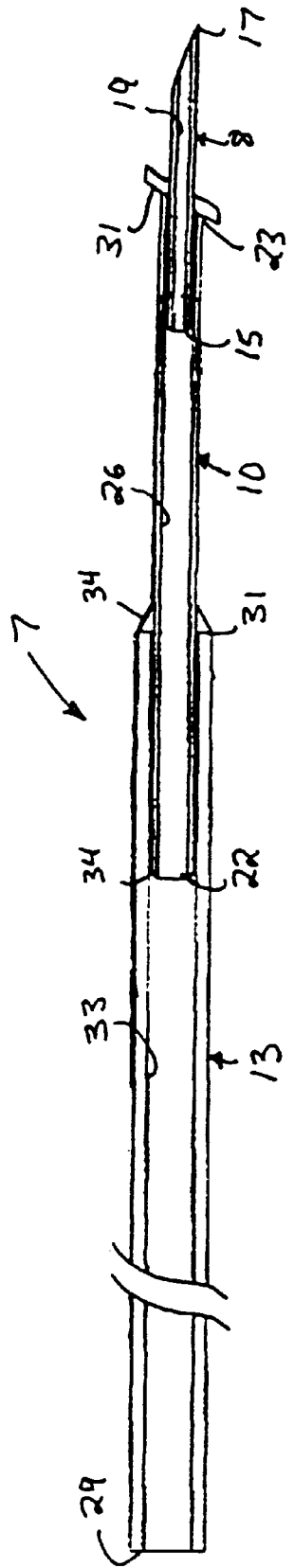
FIG. 1 illustrates a transition-bore needle apparatus for use in the treatment of urinary incontinence in accordance with the present invention.

Referring more particularly to the drawings, FIG. 1 illustrates a transition-bore needle apparatus 7 adapted for use in applications such as urethral injections, and having a distal needle 8, an intermediate tube 10, and a proximal tube 13. Transition-bore needle apparatus 7 is an element of an injection apparatus, as disclosed herein. It is to be understood that, as used herein, the term "proximal" means the end or part nearest to the operator of the instrument and the term "distal" means the end or part furthest from the operator. Thus, the front end of the instrument that enters the body canal is the distal end.

The distal needle 8 comprises a proximal end 15, a distal end 17, and a lumen 19 extending from the proximal end 15 to the distal end 17. The distal end 17 of the distal needle 8 preferably comprises a cutting edge needle tip, which is suitable for puncturing skin and other soft tissues such as muscle tissue. In an alternative embodiment, the distal end 17 of the distal needle 8 may comprise a round point needle tip for use in connection with more delicate surgical operations. The intermediate tube 10 comprises a proximal end 22, a distal end 23, and a lumen 26 extending from the proximal end 22 to the distal end 23. The proximal tube 13 comprises a proximal end 29, a distal end 31, and a lumen 33 extending from the proximal end 29 to the distal end 31.

As presently embodied, the distal needle 8, the intermediate tube 10, and the proximal tube 13 all comprise surgical stainless steel, such as 304 grade surgical stainless steel or 316 grade surgical stainless steel. In accordance with one embodiment of the present invention, at least two needles (e.g., the distal needle 8 and the intermediate tube 10) are attached from larger to smaller diameter so as to create a transitional cone to facilitate the movement of viscous bulking material, such as material containing suspended beads or micro-spheres, through the transition-bore needle apparatus in a direction from the larger diameter tube to the smaller diameter needle. In the presently preferred embodiment, three needles (i.e., the distal needle 8, the intermediate tube 10 and the proximal tube 13) are attached, preferably using an adhesive 34, from larger to smaller diameters so as to create a transitional cone to facilitate the movement of viscous materials through the transition-bore needle apparatus in a direction from the larger diameter needle to the smaller diameter needles. Other modified embodiments may incorporate a greater number of needles.

The lumen of the transition-bore needle apparatus 7 comprises both a portion of the lumen 19 of the distal needle 8 and a portion of the lumen 26 of the intermediate tube 10, as can be seen in FIG. 1. A juncture thus exists within the lumen of the transition-bore needle apparatus 7, where the diameter thereof transitions from a diameter of the intermediate tube 10 to a diameter of the distal needle 8. At this juncture, the proximal end 15 of the distal needle 8 terminates within the lumen 26 of the intermediate tube 10.

In the illustrated embodiment, the distal needle 8 comprises an inner diameter of about 0.008 inches and an outer diameter of about 0.016 inches. The distal needle 8 fits into the intermediate tube 10, which in the illustrated embodiment comprises an inner diameter of about 0.020 inches and an outer diameter of about 0.028 inches. In the presently preferred embodiment, the distal needle 8 protrudes distally about 3 mm from the intermediate tube 13. The intermediate tube 10 fits into the proximal tube 13, which as presently embodied comprises an inner diameter of about 0.50 inches, an outer diameter of about 0.032 inches, and a length of about 12 inches. The proximal tube 13 encloses the proximal end 22 of the intermediate tube 10. The proximal tube 13 preferably comprises three hypotubes, which may facilitate a tighter fit around the intermediate tube 10 and/or greater rigidity of the proximal tube 13.

A tissue stop 31 is preferably disposed about the distal needle 8 next to the distal end 23 of the intermediate tube 10. The tissue stop 31 preferably comprises a diameter, which is about the same as the diameter of the proximal tube 13. In alternative embodiments, other diameters may be constructed. The tissue stop 31 preferably comprises a circular perimeter, but may have oval or rectangular perimeters in alternative embodiments. The tissue stop 31 preferably comprises a polymeric material, which is more flexible than, for example, stainless steel. In modified embodiments, the tissue stop 31 may comprise surgical stainless steel.

An angle between a plane of the tissue stop 31 and a longitudinal axis of the transition-cone needle assembly 7 is preferably less than ninety degrees and, preferably, less than about seventy-five degrees and, more preferably, about sixty degrees as shown in FIG. 1. The orientation of the tissue stop 31 is preferably selected so that a planar surface of the tissue stop will align longitudinally with the axis of the particular lumen that is being treated. In other words, a planar surface of the tissue stop 31 should rest flat on the surface of the tissue that is to be treated with the distal needle 8. The tissue stop 31 will help to prevent the needle from penetrating deeper into the tissue than is required or desired. A surgeon performing an injection procedure using, for example, a cystoscope or the device disclosed in U.S. patent application Ser. No. 09/825,484, entitled URETHRA SURGICAL DEVICE, can view the tissue stop 31 for assistance in performing the injection at the proper angle and at the proper depth.

In a modified embodiment of the apparatus, the tissue stop 31 may be omitted so that only the difference in outer diameters between the distal needle 8 and the intermediate tube 10 effectively operate as a tissue stop. In yet another modified embodiment, the tissue stop can be secured about the intermediate tube 10, instead of being secured about the distal needle 8, so that a distal planar surface of the tissue stop is flush with the distal end 23 of the intermediate tube 15.

According to another aspect of the present invention, the proximal end 22 of the intermediate tube 10 is beveled to improve a flow of viscous material through the lumen of the transition-bore needle apparatus 7. FIG. 1A is a cross-sectional view of a proximal end 22 with edges beveled at a 45 degree angle from the longitudinal axis of the distal needle 8. The beveling may be performed by filing an initially square outer edge to an angle less than ninety degrees and, preferably, less than sixty degrees, and more preferably, about forty-five degrees. After the proximal end 22 of the intermediate tube 10 is beveled, the intermediate tube 10 is then secured within the lumen 33 of the proximal tube 13, through the application of adhesive material between the outer surface of the intermediate tube 10 and inner surface of the proximal tube 13 at their contacting surfaces. In modified embodiments, the angle may be reduced to, for example, 30 degrees or even about 15 degrees from the longitudinal axis of the intermediate tube 10.

In accordance with another aspect of the present invention, the proximal end 22 of the intermediate tube 10 is chamfered to improve a flow of viscous material through the lumen of the transition-bore needle apparatus 7. FIG. 1B is a cross-sectional view of a proximal end 22 with edges chamfered at a 45 degree angle from the longitudinal axis of the distal needle 8. The chamfering may be performed by filing an initially square edge on the interior side of the tubing to an angle less than ninety degrees and, preferably, less than sixty degrees, and more preferably, about forty-five degrees. In modified embodiments, the angle may be reduced to, for example, 30 degrees, or even about 15 degrees from the longitudinal axis of the distal needle 8.

In yet another aspect of the present invention, the proximal end 22 of the intermediate tube 10 is both chamfered and beveled, in accordance with the structures discussed in the preceding paragraphs, to thereby improve a flow of viscous material through the lumen of the transition-bore needle apparatus 7. The proximal end 15 of the distal needle 8 is preferably beveled and/or chamfered, similarly to that described above in connection with the proximal end 22 of the intermediate tube 10. In modified embodiments, only the proximal end 15 of the distal needle 8 is beveled and/or chamfered, and the proximal end 22 of the intermediate tube 10 is neither beveled nor chamfered.

Figure 2A:
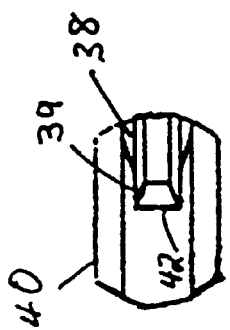
FIG. 2A is a cross-sectional view of a proximal end of a needle with edges chamfered at about a 30 degree angle from the longitudinal axis of the needle.
Figure 2B:
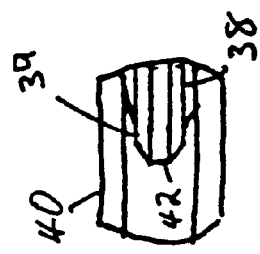
FIG. 2B is a cross-sectional view of a proximal end of a needle with edges beveled at about a 30 degree angle from the longitudinal axis of the needle.
Figure 2:
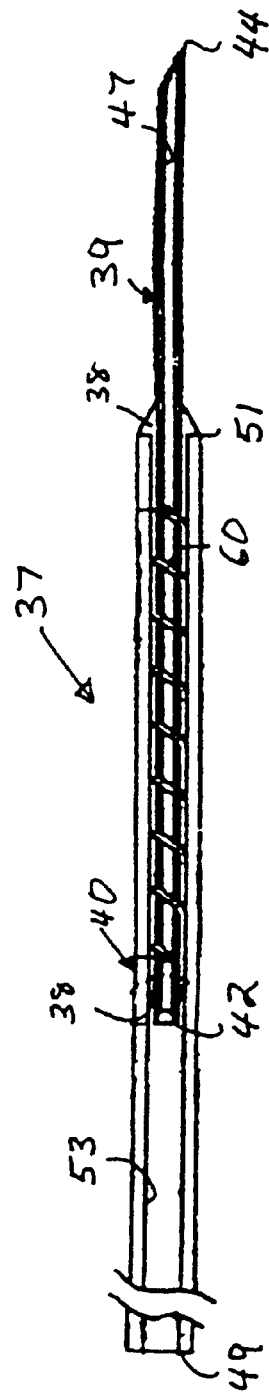
FIG. 2 illustrates a transition-bore needle apparatus for used in the treatment of gastro-esophageal reflux disease in accordance with the present invention.

Turning now to FIG. 2, a transition-bore needle assembly 37 is illustrated for use in applications such as lower esophageal injections of bulking material. The transition-bore needle assembly 37 comprises a needle 39 connected to a flexible tube 40. The flexible tube 40 may comprise a polymeric material, such as polyethylene terephthalate (PET). The needle 39 comprises a proximal end 42, a distal end 44, and a lumen 47 extending between the proximal end 42 and the distal end 44. The distal end 44 of the needle 44 preferably comprises a cutting edge needle tip, which is suitable for puncturing skin and other soft tissues such as muscle tissue. As presently embodied, the cutting edge needle tip is formed at a 20 degree angle from a longitudinal axis of the needle 39. In an alternative embodiment, the distal end 44 of the needle 39 may comprise a round point needle tip. The flexible tube 40 similarly has a proximal end 49, a distal end 51, and a lumen 53 extending from the proximal end 49 to the distal end 51.

As presently embodied, the needle 39 comprises surgical stainless steel, such as 304 grade surgical stainless steel or 316 grade surgical stainless steel. The proximal end 42 of the needle 39 is inserted into and attached to the distal end 51 of the flexible tube 40, so as to create a transitional cone to facilitate the movement of viscous bulking material, such as material containing suspended beads or micro-spheres, through the transition-bore needle apparatus 37 in a direction from the flexible tube 40 to the needle 39. The lumen of the transition-bore needle apparatus 37 comprises both a portion of the lumen 47 of the needle 39 and a portion of the lumen 53 of the flexible tube 40, as can be seen from FIG. 2. A juncture thus exists within the lumen of the transition-bore needle apparatus 37, where the diameter thereof transitions from a diameter of the flexible tube 40 to a diameter of the needle 39. At this juncture, the proximal end 42 of the needle 39 terminates within the lumen 53 of the flexible tube 40.

In the illustrated embodiment, the needle 39 has an inner diameter of about 0.012 inches and an outer diameter of about 0.020 inches, and the flexible tube 40 has an inner diameter of 0.032 inches and an outer diameter of 0.056 inches. A wire 60 is wrapped around the needle 39 and glued into place. In the gluing process, the glue 38 is preferably allowed to dry and then heat cured. Another glue is then applied to the surfaces of the resulting wire 60 and needle 39. The glue may comprise, for example, a lock-tight glue or a superglue. The needle 39 is then gripped and held with, for example, a chuck, and screwed into the flexible tube 40, which may comprise a polymeric tube having, for example, a smooth inner surface. Some glue will remain on the distal end 51 of the flexible tube 40 to form a seal, after the needle 39 and wire 60 are screwed in. The wire 60 around the needle 39 preferably deforms the smooth inner surface of the flexible tube 40 for a frictional fit.

According to another aspect of the present invention, the proximal end 42 of the needle 39 is beveled to improve a flow of viscous material through the lumen of the transition-bore needle apparatus 37. FIG. 2A is a cross-sectional view of a proximal end 42 with edges chamfered at about a 30 degree angle from the longitudinal axis of the distal needle 39. The beveling may be performed by filing an initially square edge to an angle less than ninety degrees and, preferably, less than sixty degrees, and more preferably, about forty-five degrees. After the proximal end 42 of the needle 39 is beveled and/or chamfered, the needle 39 is secured within the lumen 53 of the flexible tube 40. In modified embodiments, the angle may be reduced to, for example, 30 degrees or about 15 degrees.

In accordance with another aspect of the present invention, the proximal end 42 of the needle 39 is chamfered to improve a flow of viscous material through the lumen of the transition-bore needle apparatus 37. FIG. 2B is a cross-sectional view of a proximal end 42 with edges chamfered at about a 30 degree angle from the longitudinal axis of the distal needle 39. The chamfering may be performed by filing an initially square edge to an angle less than ninety degrees and, preferably, less than sixty degrees, and more preferably, about forty-five degrees. In modified embodiments, the angle may be reduced to, for example, 30 degrees, or even about 15 degrees. According to yet another aspect of the present invention, the proximal end 42 of the needle 39 is both chamfered and beveled, in accordance with the structures discussed in this preceding paragraph, to thereby improve a flow of viscous material through the lumen of the transition-bore needle apparatus 37.

Figure 3:
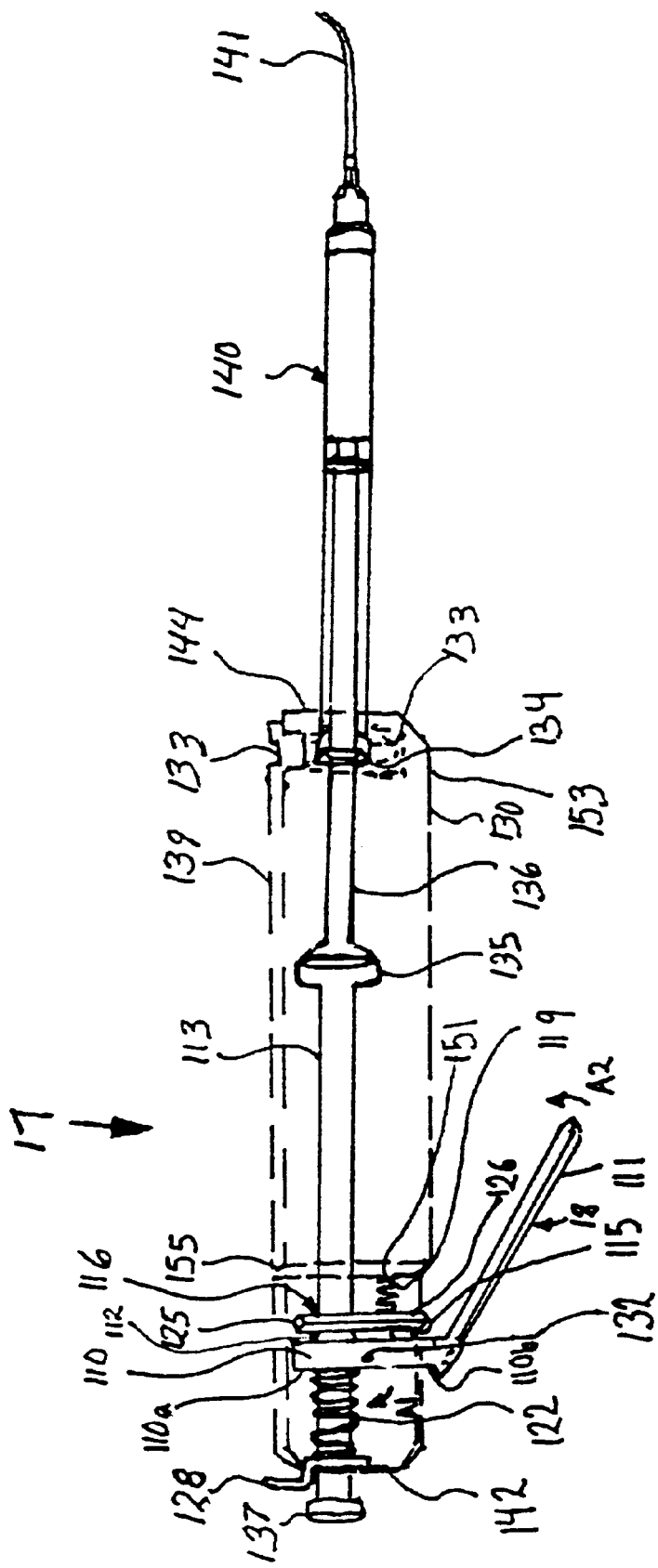
FIG. 3 illustrates an injection facilitation apparatus with an attached syringe for use with a transition-bore needle apparatus.

FIG. 3 illustrates an injection facilitation apparatus 17 for use with the injection apparatus of the present invention. Injection facilitation apparatus 17 may be used with the transition-bore needle apparatus disclosed hereinabove. The housing 130 preferably comprises a molded polymeric material, generally in the shape of a hollow cylinder. In modified embodiments, other materials and shapes may be used. In the illustrated embodiment, the housing 130 comprises a proximal end 142, a distal end 144, a first side 139 and a second side 153.

Figure 4:
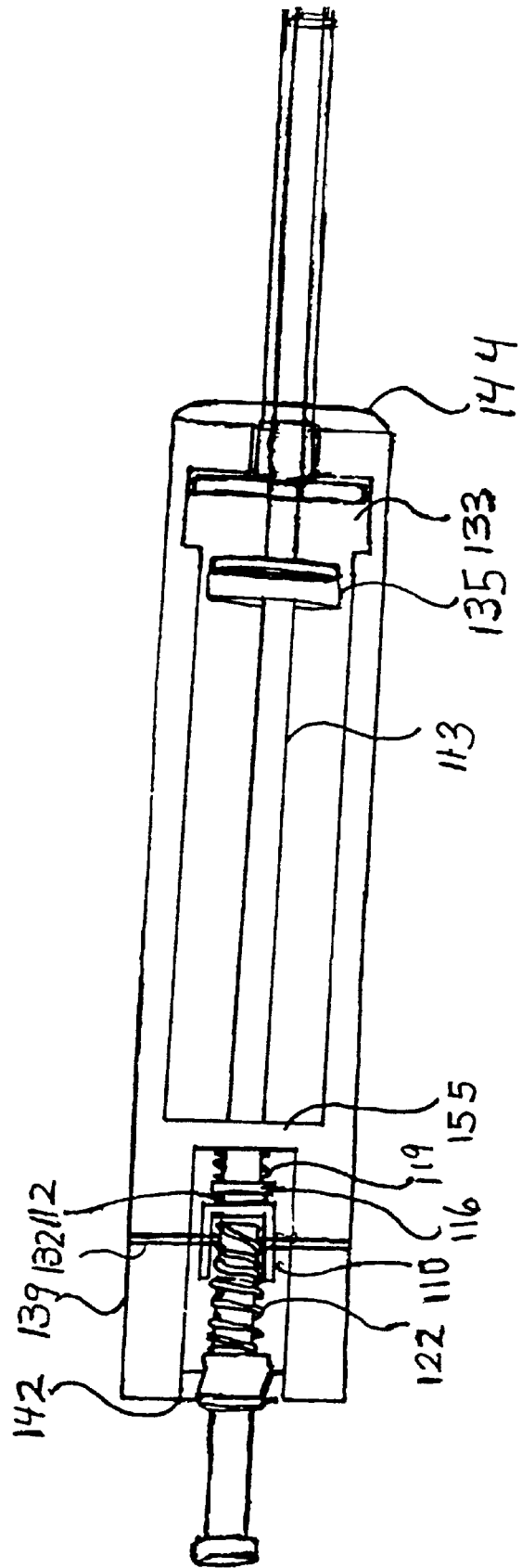
FIG. 4 shows a part cross-sectional view of the injection facilitation apparatus, showing the housing and its internal components.
Figure 5:
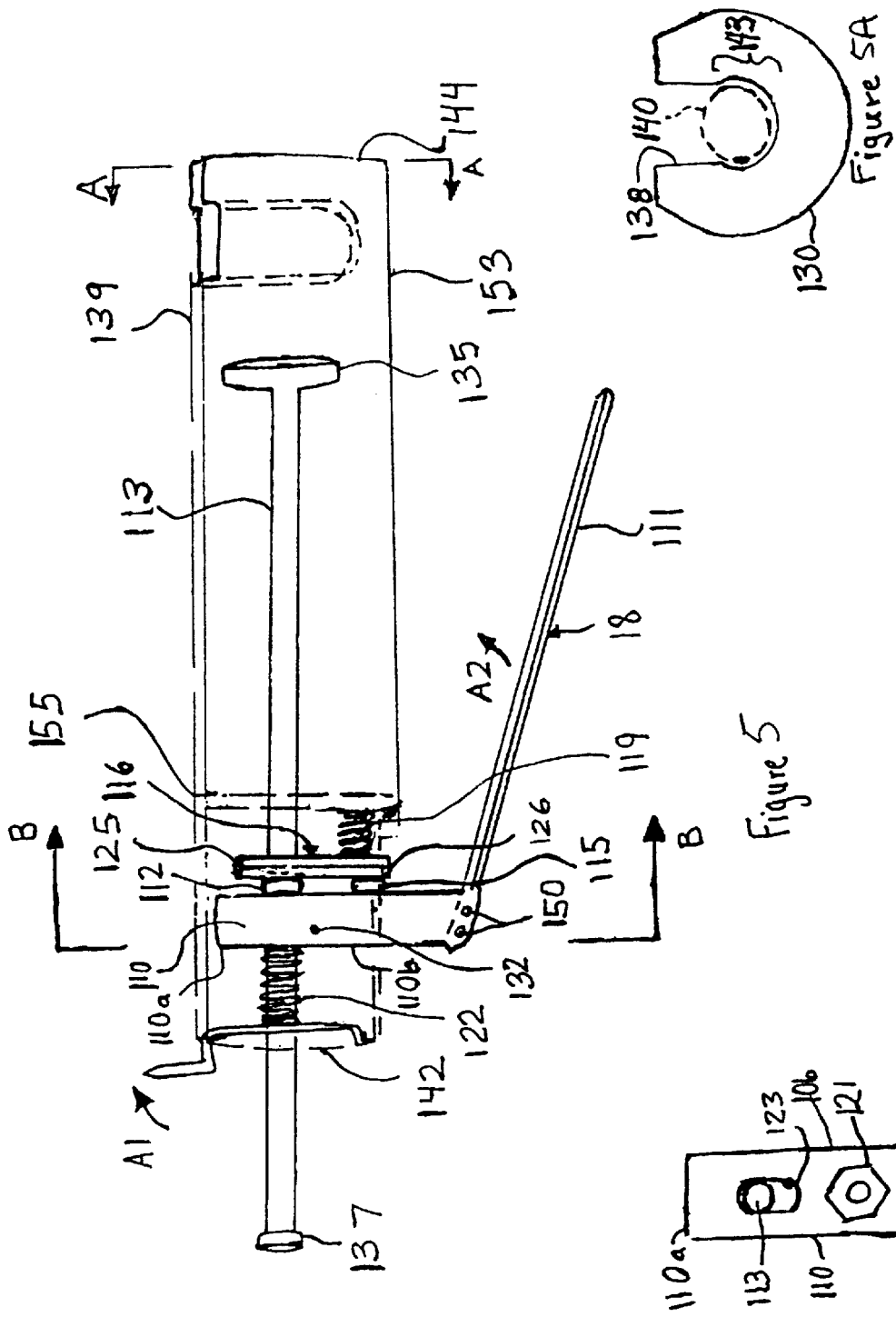
FIG. 5 is a part cross-sectional view of the injection facilitation apparatus wherein the handle is in a neutral position with no external force being applied to the handle.

FIGS. 4 and 5 are additional views of the injection facilitation apparatus 17. A portion of the housing 130 is preferably removed on the first side to accommodate a syringe 140 therein. In modified embodiments, other means, such as a hinged door, may be incorporated for accommodating the syringe 140 into the housing 130. The housing 130 comprises a slot 133, extending in a direction from the first side to the second side into the housing and being configured to accommodate and hold a finger rest 134 of the syringe 140 within the housing. An end view of the housing 130, taken in the direction of the arrow A—A of FIG. 5, is shown in FIG. 5A. A slot 138 is disposed at the distal end 144 of the housing 130 for accommodating the syringe 140 therein. The slot 138 extends from the first side 139 of the housing in a direction toward the second side 153, and terminates with a circular or rounded portion 143 for accommodating and holding the syringe 140.

A movable rod 113 extends within the housing 130 from the proximal end 142 to the distal end 144 (in accordance with a fully extended position of the rod 113). When the rod 113 pushes distally against the syringe 140, the syringe 140 will tend to move in the distal direction. The finger rest 134 of the syringe 140, however, will press distally against the slot 133, to thereby prevent distal movement of the syringe 140. Thus, only the plunger 136 of the syringe 140 will move distally under the distal force of the rod 113. Distal movement of the plunger 136, relative to the rest of the syringe 140, will result in the plunger 136 expelling a portion of the syringe contents, which may comprise a viscous bulking agent, from the syringe 140 and into the elongate catheter 141.

The elongate catheter 141 preferably comprises a length sufficient to extend through the relevant body passage and to the site of operation. For example, the elongate catheter 141 may be constructed to have a length sufficient to extend through a cystoscope for operation on the urinary sphincter near the bladder. As another example, the elongate catheter 141 may be configured to have a length (e.g., about one meter) sufficient to extend through a gastroscope for operation on the lower esophageal sphincter near the stomach. The elongate catheter 141 may comprise or be connected to the flexible tube 13 of FIG. 1 or the proximal tube 40 of FIG. 2.

The force required for delivery of a viscous fluid through the elongate catheter 141 and to the target site of injection will be proportionate to the length and cross-sectional area of the elongate catheter 141. This force required to deliver the viscous material through the lumen of the elongate catheter will thus increase as the length of the elongate catheter increases, and further will increase as the cross-sectional area of the elongate catheter is decreased.

The injection facilitation apparatus 17 of the present invention facilitates the injection of viscous filler materials, and provides for increased accuracy in the amounts of such dispensed materials. An exemplary embodiment of the invention comprises an injection facilitation apparatus for use in conjunction with a needle tip stainless steel elongate catheter that can be introduced through a patient's urethra in the treatment of urinary incontinence. As another example, a treatment for gastro-esophageal reflux disease may be fashioned to increase the strength or length of the lower esophageal sphincter (LES) via the deposition of a viscous bulking material into surrounding tissues of the lower esophageal sphincter. An injection facilitation apparatus of the present invention is suitable for such use in conjunction with a needle tip, flexible, polymeric elongate catheter. The viscous suspension can be injected via a syringe and needle directly into the specific areas where the viscous agent is desired. Principal uses of the present invention are to accurately and conveniently dispense the viscous material to thereby alter the operational architecture of the patient's sphincter. Thus, the bio-mechanical characteristics of the sphincter are altered to alleviate the disorder.

As shown in FIG. 3, a fastener 128 comprises an aperture for accommodating the rod 113 therethrough, and is biased proximally against an inner surface of the proximal end 142 of the housing 130. In the illustrated embodiment, the fastener 28 comprises surgical stainless steel. A handle spring 122 is disposed about the rod 113 between an internal end 110 of a pivot arm 18 and the fastener 128. In addition to comprising an internal end 110, the pivot arm 18 further comprises a handle end 111. The handle spring 122 provides a proximal biasing force against the fastener 128 and a distal biasing force against the internal end 110 of the pivot arm 8. The handle spring 122 may comprise, for example, surgical stainless steel.

It can be seen from the figure that the handle spring 122 biases an internal first end 110a of the pivot arm 18 distally, and the driving spring 119 biases an internal second end 110b of the pivot arm 18 proximally. The combination of the handle spring 122 and the driving spring 119 tend to rotate the pivot arm 18 about the pivot pin 132 in the clockwise direction shown by the arrow A1. An inward thrust by the hand of a user on the handle end 111 of the pivot arm 18 causes the pivot arm 18 to rotate about the pivot pin 132 in the direction of the arrow A2. As the pivot arm 18 pivots about the pivot pin 132, the internal first end 110a of the pivot arm 18 moves generally in a proximal direction and the internal second end 110b of the pivot arm 18 moves generally in a distal direction. When the internal second end 110b of the pivot arm 18 moves distally in response to the handle end 111 moving in the direction of the arrow A2, the screw head 115, which is secured to the internal second end 110b, applies a distal force against the biased end 126 of the of the driving arm 116.

In the illustrated embodiment, the handle end 111 is attached to the internal end 110 via two small identical screws 150 (FIG. 5), and the internal end 110 rests on the handle spring 122. As can be seen best in FIG. 3, a pivot pin 132, preferably comprising a surgical stainless steel bar, passes through both the housing 130 and the internal end 110 of the pivot arm 18. The pivot arm 18 thus pivots about the pivot pin 132 in both clockwise and counter-clockwise directions, as shown in FIG. 3 by the arrows A1 and A2, respectively.

A ring 112, which preferably comprises surgical stainless steel, is disposed around the rod 113 between the internal end 110 and a driving arm 116. The ring 112 preferably comprises a loosely fitted and movable stainless steel washer. The driving arm 116, preferably comprising stainless steel, rests on top of the ring 112. In between the driving arm 116 and the internal end 110 also rests a screw head 115, positioned on a distal side of the internal end 110. The screw head 115 is secured onto the internal end 110 of the pivot arm 18 with a nut 121, as can be seen from FIG. 5b. Distally of the driving arm 116 rests the driving spring 119, which is held in place by an alignment protrusion 151 that preferably comprises a knob (not shown) formed on a housing wall 155 of the housing 130

The rod 113 extends through the fastener 128, the handle spring 122, the pivot arm 18, the ring 112, and driving arm 116. The internal end 110 of the pivot arm 18 and the driving arm 116, in combination with the fastener 128, work together to provide slidable alignment to the rod 113. The rod 113 comprises a proximal rod disk 137 connected at a proximal end of the rod 113 and a distal rod disk 135 connected at a distal end of the rod 113. As presently embodied, the rod 113 is removably attached to at least one of the proximal rod disk 137 and the distal rod disk 135. In the illustrated embodiment, the rod 113 is permanently secured to or integrally formed with the proximal rod disk 137 and is removably connected (e.g., threaded) to the distal rod disk 135.

The injection facilitation apparatus 17 contains a pivot mechanism that forces the rod 113 distally within the housing 130 toward the slot 133, where the syringe 140 is held and positioned, as illustrated in FIG. 3. A clear depiction of the slot 133 can be seen in FIG. 4. When the syringe 140 is positioned within and held by the housing 130, a base of the syringe, plunger 136, rests flat against the distal rod disc 135.

FIGS. 3–5 depict the injection facilitation apparatus 17 at rest, wherein no external force is applied to the handle end 111 of the pivot arm 18. In the relaxed or resting position of FIGS. 3–5, there is no gap between the driving arm 116 and the ring 112, which rests on the internal end 110 of the pivot arm 18. It can be seen from the figure that without an external force applied to the handle end 111 of the pivot arm 18, the internal end 110 of the pivot arm 18 rests between the handle spring 122 and a combination of the ring 112 and the driving arm 116. The handle spring 122 biases an internal first end 110a of the pivot arm 18 distally, and the driving spring 119 biases an internal second end 110b of the pivot arm 18 proximally.

The combination of the handle spring 122 and the driving spring 119 tend to rotate the pivot arm 18 about the pivot pin 32 in the clockwise direction shown by the arrow A1. However, in accordance with an aspect of the present invention, a rotation-limiting structure prevents the pivot arm 18 from rotating clockwise past the orientation shown in FIG. 3 and FIG. 5. For this reason, the orientation of the pivot arm 18 shown in, for example, FIG. 3 is referred to as being in the relaxed position. Application of a force by the hand of an operator to pivot the handle end 111 of the pivot arm 18 in the counter-clockwise direction shown by arrow A2 will move the assembly out of the relaxed position and move the rod 113 distally.

Regarding the rotation-limiting structure and with reference to FIG. 5, the handle spring 122 applies a distal force onto the internal first end 110a, resulting in the generation of a rotational force or moment arm on the internal end 110 which would cause the internal end 110 to rotate about the pivot pin 132 in the direction of the arrow A1. If the pivot pin 132 were to rotate in the direction of the arrow A1, the internal first end 110a would pivot distally about the pivot pin 132 and the internal second end 110b would pivot proximally about the pivot pin 132. When the internal end 110 of the pivot arm 18 is in the resting position as shown in FIGS. 3–5, however, an aperture 123, which is disposed on the internal end 110 of the pivot arm 18 for accommodating the rod 113 therethrough, prevents rotation in the direction of the arrow A1. An end view of the internal end 110, taken in the direction of the arrow B—B of FIG. 5, is shown in FIG. 5B. The aperture 123, which serves as a rotation-limiting structure, is shaped to (1) allow pivoting of the internal end 110 from the position shown in FIGS. 3–5 in the direction of the arrow A2, and (2) prevent pivoting of the internal end 110 from the position shown in FIGS. 3–5 in the direction of the arrow A1.

More particularly, the aperture 123 comprises an elongate shape having a width that is about the same dimension as a diameter of the rod 113 passing through the aperture 123, and having a length that is appreciably greater than the diameter of the rod 113 passing through the aperture 123. For example, the length should be at least 1.25 times the diameter of the rod 113 passing through the aperture 123 and, preferably, should be at least about 1.5 times, and more preferably, should be about 2 times the diameter of the rod 113 passing through the aperture 123.

Now, regarding the orientation of the aperture 123 relative to the rod 113 passing therethrough, in the position shown in FIG. 5 the portion of the aperture 123 closest to the internal first end 110a of the pivot arm 18 contacts the rod 113 to prevent further movement of the pivot arm 18 in the direction of the arrow A1. However, in the same position shown in FIG. 5, the portion of the aperture 123 closest to the internal second end 110b of the pivot arm 18 does not contact and is spaced from the rod 113 to facilitate movement of the pivot arm 18 in the direction of the arrow A2. Thus, the engagement of the portion (e.g., edge) of the aperture 123 closest to the internal first end 110a with the rod 113 serves to limit rotational movement of the pivot arm 18 in the direction of the arrow A1. In modified embodiments, other constructions may be used to limit rotational movement of the pivot arm 18 in the direction of the arrow A1, such as a protrusion on the second side 153 of the housing 130 to contact the internal second end 110b and prevent that end from moving proximally from the position shown in FIG. 5.

Figure 6:
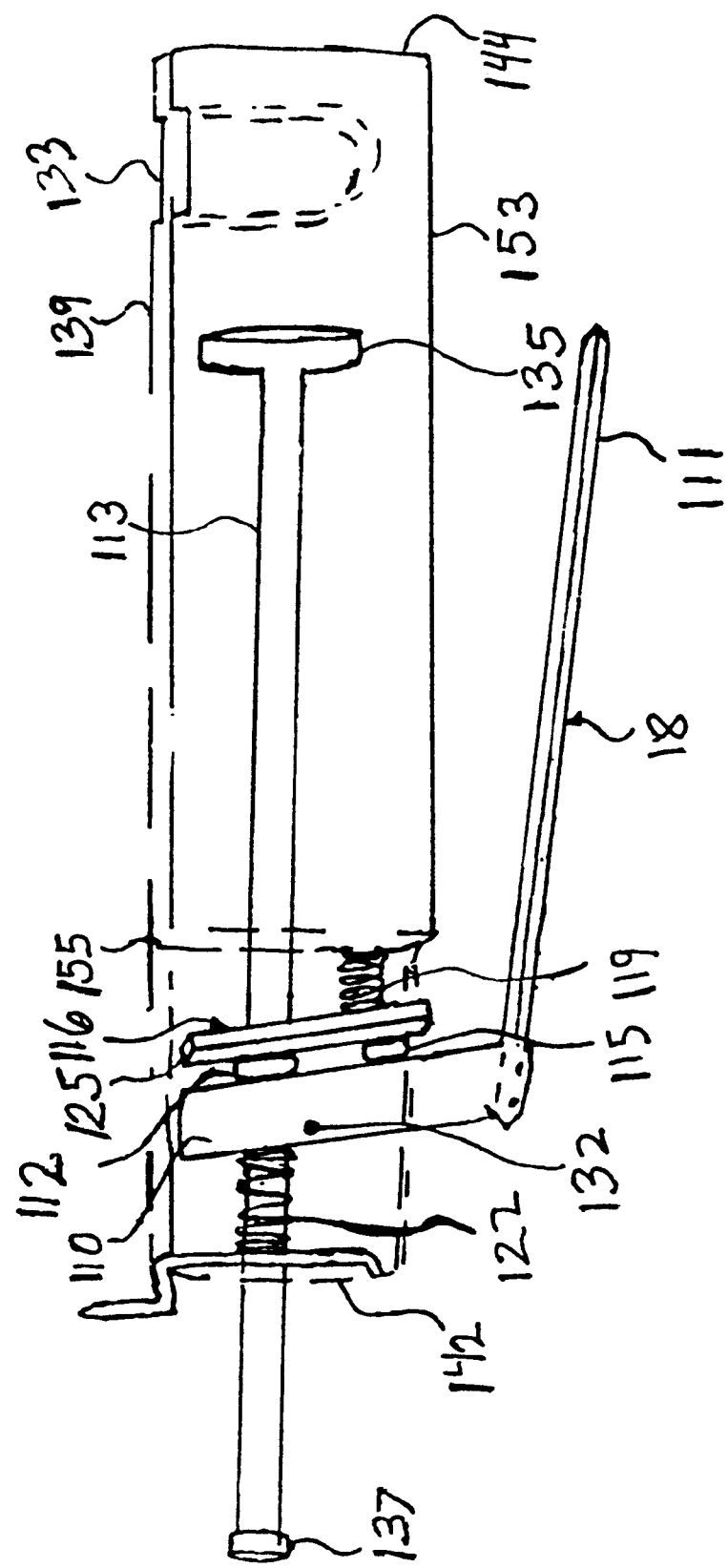
FIG. 6 is a part cross-sectional view of the injection facilitation apparatus of FIG. 5 after an initial application of external force has been applied to the handle.
Figure 7:
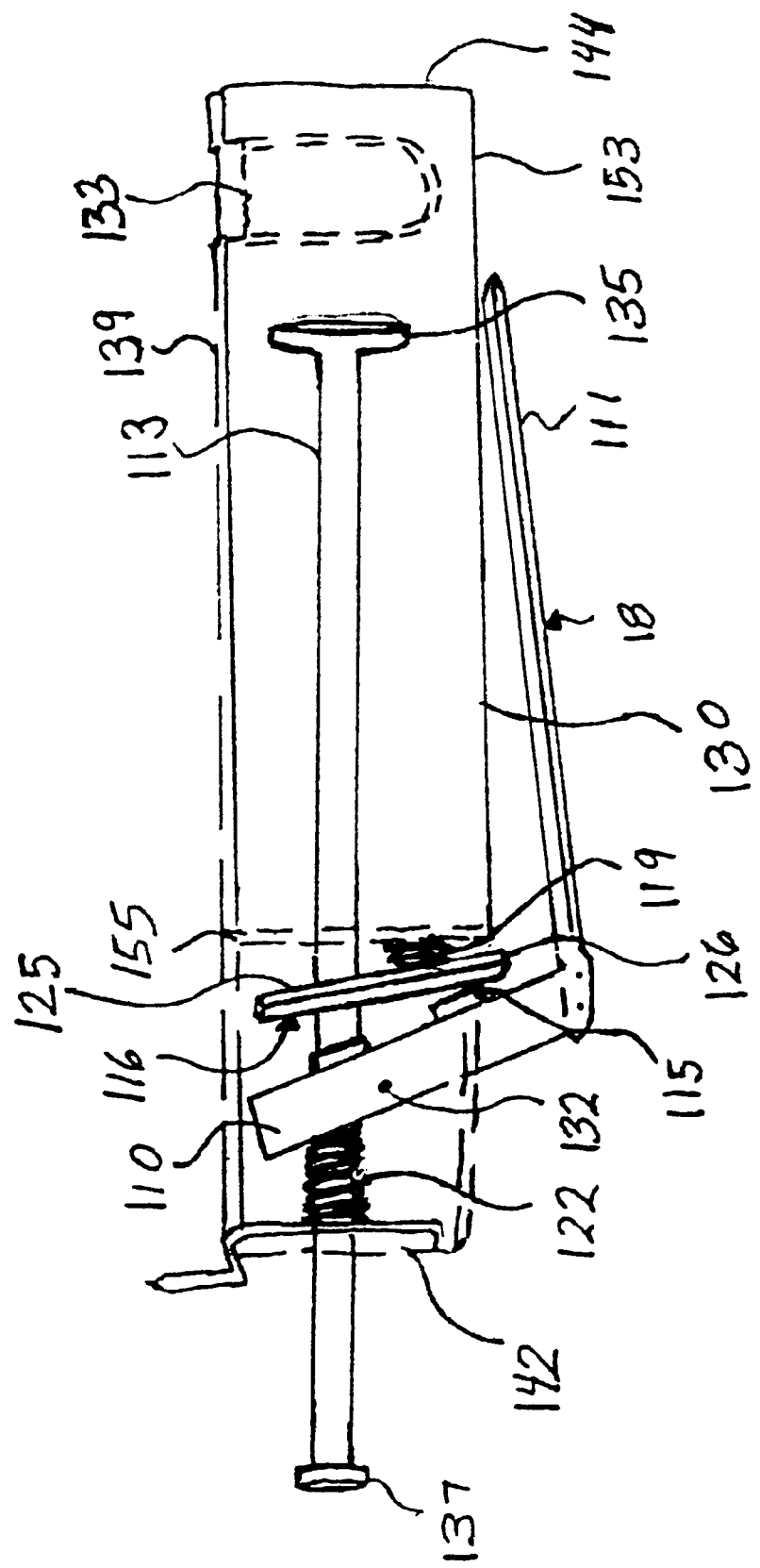
FIG. 7 illustrates the injection facilitation apparatus of FIG. 5 at a time of maximum application of external force to the handle.

The effect of a pivoting force applied by the hand of a user on the pivot arm 18 of the injection facilitation apparatus 17 can be seen through a comparison of FIGS. 5–7. An inward thrust by the hand of a user on the handle end 111 of the pivot arm 18 causes the pivot arm 18 to rotate about the pivot pin 132 in the direction of the arrow A2. As the pivot arm 18 pivots about the pivot pin 132, the internal first end 110*a* of the pivot arm 18 moves generally in a proximal direction and the internal second end 110*b* of the pivot arm 18 moves generally in a distal direction. When the internal second end 110*b* of the pivot arm 18 moves distally in response to the handle end 111 moving in the direction of the arrow A2, the screw head 115, which is secured to the internal second end 110*b*, applies a distal force against the biased end 126 of the of the driving arm 116.

As the screw head 115 moves generally distally, while rotating about the pivot pin 132, the screw head 115 slides against the driving arm 116 in a direction toward the rod 113. The component of movement of the screw head 115 in the distal direction, as it slides on the driving arm 116, moves the biased end 126 of the driving arm 116 distally against the proximal bias of the driving spring 119. The changes in position of the pivot arm 18 and the driving arm 116 can be seen through the progression of FIGS. 5–7.

The initial distal movement of the screw head 115 is applied to the biased end 126 of the driving arm 116, which generates a moment arm. The moment arm tends to cause the driving arm 116 to pivot generally in the direction of the arrow A2 and generally about a pivot point defined by the interaction of the rod 113 and the driving arm 116.

A rod-clamping end 125 of the driving arm 116 comprises an aperture for accommodating the rod 113 therethrough. The cross-sectional area of the aperture is shaped to be slightly larger than the cross-sectional area of the rod 113, so that the rod 113 can freely move through the aperture when the driving arm 116 is oriented at a predetermined orientation (corresponding, for example, to an orientation when the pivot arm 18 is in the relaxed position). As presently embodied, the rod 113 can freely move through the aperture of the driving arm 113, with little or reduced friction relative to other orientations, when the driving arm 113 is substantially perpendicular to an axis of the rod 113. In modified embodiments, other angular positions may be implemented.

As the driving arm 116 moves under the influence of the screw head 115 from its perpendicular orientation in an approximate direction of the arrow A2, biased end 126 of the driving arm 116 will move slightly distally so that the orientation of the driving arm 116 changes and so that the rod 113 can no longer freely slide (or slide with reduced friction) through the aperture of the driving arm 116. Thus, the clamping end 125 of the driving arm 116 will be somewhat locked onto the rod 113 at the angle of contact (which as presently embodied is an angle of about one to a about five degrees from 90 degrees). At this position, shown in FIG. 6, there will be a small gap between internal end 110 and driving arm 116.

Further movement of the handle end 111 in the direction of the arrow A2 is depicted in FIG. 7. During this extended push on pivot arm 18 the distance between internal end 110 and driving arm 116 will increase to its maximum separation. The screw head 115 continues to move the driving arm 116 distally. Since the driving arm 116 has already rotated slightly to clamp the rod 113, the driving arm 116 will not rotate further as the screw head 115 pushes further and further distally against the driving arm 116. Thus, continued movement of the screw head 115 against the driving arm 116 moves the driving arm 116, which in turn moves the clamped rod 113 forward.

As the driving arm 116 moves forward, the driving spring 119 is compressed against the housing wall 155, and the handle spring 122 is compressed proximally against the fastener 128 by proximal movement of the internal first end 110*a*. In the illustrated embodiment, movement of the pivot arm 18 in the direction of the arrow A2 will cease when the handle end 111 contacts the surface of the housing 130.

In modified embodiments of the invention the length of the internal end 110 can be altered. Varying the length of the internal end 110 can vary the amount of material expelled from the catheter-syringe within the injection facilitation apparatus. For example, the internal end 110 can be lengthened such that the new added length protrudes out of the housing on the second side 153, which will cause a proportional increase in the range of movement of the handle end 111. In accordance with another modification, the angle formed between the handle end 111 and the internal end 110 can be increased so that the handle end 111 can be moved further in the direction of the arrow A2 for a corresponding greater movement of the rod 113. In accordance with one aspect of the present invention, the injection facilitation apparatus is engineered so that a full compression of the handle end 111 will eject an exact amount of filler material, such as a specific volume amount to generate one mucosa bulge near a urinary sphincter.

As the angle between the handle end 111 and the internal end 110 increases, the amount of distance created between the internal end 110 and the driving arm 116 at maximum compression of the handle end 111 is also intensified. This translates into a greater range of push movement on the rod 113, and thus a greater amount of viscous material being expelled from the syringe as the plunger 136 receives the additional push from the rod 113.

In other words, the screw head 115 moves generally distally, to thereby move the biased end 126 of the driving arm 116 distally against the proximal bias of the driving spring 119. The initial distal movement of the screw head 115 is applied to the biased end 126 of the driving arm 116, which generates a moment arm. The moment arm tends to cause the driving arm 116 to pivot generally in the direction of the arrow A2 and generally about a pivot point defined by the interaction of the rod 113 and the driving arm 116. As the driving arm 116 moves under the influence of the screw head 115 from its perpendicular orientation in an approximate direction of the arrow A2. The biased end 126 of the driving arm 116 will move slightly distally so that the orientation of the driving arm 116 changes and so that the rod 113 can no longer freely slide (or slide with reduced friction) through the aperture of the driving arm 116. Thus, the clamping end 125 of the driving arm 116 will be somewhat locked onto the rod 113 at the angle of contact (which as presently embodied is an angle of about one to a about five degrees from 90 degrees). Continued movement of the screw head 115 against the driving arm 116 moves the driving arm 116, which in turn moves the clamped rod 113 forward.

Although the injection facilitation apparatus 17 is designed to facilitate accurate dispensing of viscous materials from a syringe, such as filler materials, the injection facilitation apparatus 17 further may be used to accurately dispense other materials and fluids as well. In the illustrated embodiment, the filler material comprises collagen and/or micro-spheres, such as disclosed in U.S. Pat. No. 5,344,452, the contents of which are expressly incorporated herein by reference, or, for example, any other type of injectable bulking agent.

Another alternative embodiment would comprise a longer housing 120, with a correspondingly longer rod 113, such that the length of the rod 114 would extend proximally an additional distance equal to about a length of the handle end 111. The handle end 111 would then be attached via screws 150 to the internal end 110 in an inverted position, so that the handle end 111 extends proximally instead of distally. The handle can be formed of another shape to accommodate the different direction of action, and the mechanism of action and other components would remain substantially the same.

The injection facilitation apparatus 17 can increase the precision of dispensing fluids from the syringe 140, as it can be calibrated to permit a specific concentration of material to be dispensed from the syringe corresponding to a certain range of movement of the handle end 111. This is especially important due to the high level of viscosity of the material being passed through the syringe, the distance of the elongate catheter 141, and the general need for surgical precision when injecting bulking agents. Further, the injection facilitation apparatus 17 can facilitate effective dispensation by reducing the amount of strength or effort required to secrete the viscous material out the syringe.

The treatment for gastro-esophageal reflux disease may be fashioned to increase the strength or the length of the lower esophageal sphincter (LES) by depositing a viscous material around the lower esophageal sphincter. The suspension can be injected via a syringe and needle directly into the specific areas where the viscous agent is desired. A principal use of the exemplary embodiment is to accurately dispense the viscous material to thereby alter the physiological architecture of the patient's sphincter and adjacent tissues. Thus the bio-mechanical characteristics of the and sphincter surrounding tissues are altered to alleviate urinary incontinence and gastro-esophageal reflux.

The transition-bore needle apparatus 17 of the present invention facilitates the injection of the viscous filler material, by optimizing a flow of the viscous material at the junctions of the needles used for intraluminal injections. The transition-bore needle apparatus 17 may be used in conjunction with surgical instruments, such as endoscopes, cystoscopes, and gastroscopes, to aid in intraluminal injections of materials into body tissues within body lumens. When the body lumen comprises an esophagus, the gastroscope is inserted through the esophagus into a vicinity of the lower esophageal sphincter, and a long needle is used to inject a filler material into and adjacent to the lower esophageal sphincter tissues for the treatment of acid reflux. When the body lumen comprises a female urethra, the cystoscope is inserted through the urethra to the urinary sphincter adjacent to the bladder neck, and a long needle is used to inject a filler material into and adjacent to the urinary sphincter tissues for the treatment of stress urinary incontinence. The filler material may also be injected, for example, along a greater length of the urethra.

Figure 8:
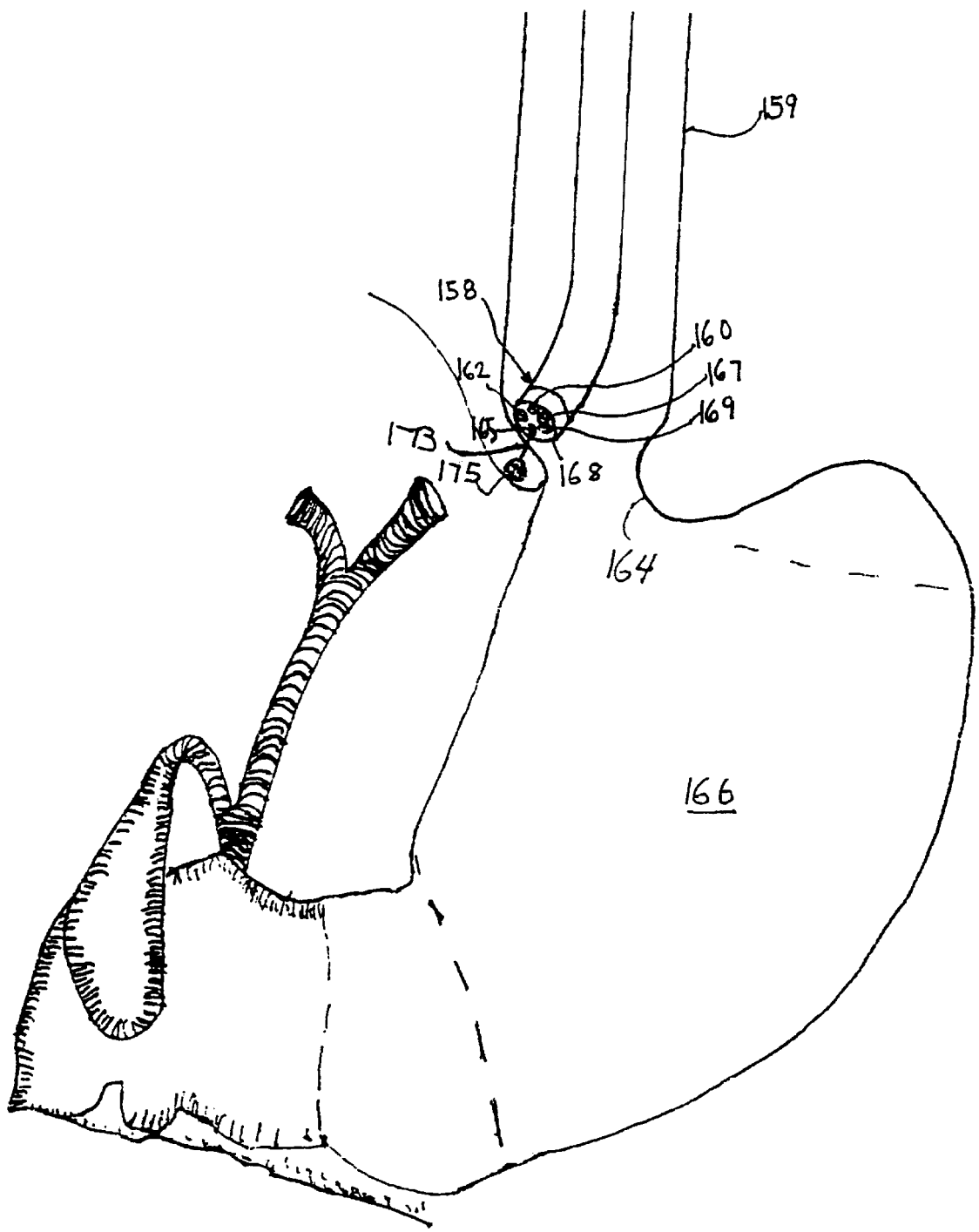
FIG. 8 illustrates a gastroscope used in the urethra to treat urinary incontinence in accordance with the present invention.

FIG. 8 illustrates a gastroscope 158 inserted through an esophagus 159 of a patient. The gastroscope 158 is positioned near the patient's lower esophageal sphincter 164 just above the body of the stomach 166. The injection facilitation apparatus 17 of the present invention is used in conjunction with a syringe and the gastroscope 158 of FIG. 8.

The gastroscope 158 in the illustrated embodiment is constructed to be flexible and to be capable of bending, for example, one hundred eighty degrees. Although other scopes and surgical devices suitable for insertion and manipulation within body passages may be used in accordance with the present invention, the presently illustrated surgical device comprises a gastroscope 158 having a flexible, cylinder body with a distal end 168 for facilitating surgical procedures within a body passage. In the illustrated embodiment, the gastroscope 158 comprises an Olympus GIF-K Gastroscope.

The distal end 168 in the illustrated embodiment comprises five openings, but as few as two openings may be incorporated in modified embodiments. An objective lens 160 is enclosed in a first one of the openings to provide a visual pathway through the lumen and of the surgical site of interest. The gastroscope 158 further comprises another opening for providing a suction and/or working channel 165. Also provided at the distal end 168 is a channel for accommodating a light guide 162, which carries light to the distal end 168 for facilitating viewing of the treatment area through the visual passageway. The light guide 162 preferably comprises a fiber optic light guide. Alternatively a LED, or other bulb, or other light source may be incorporated. A water-feeding nozzle 169, which directs pressurized water across the objective lens 160 to clear debris and an air-feeding nozzle 167 are also housed within two respective channels of the gastroscope 158. The air-feeding nozzle 167 can be used to direct pressurized air across the objective lens 160 to remove moisture and to provide, in accordance with one application, distension of the cavity being examined.

An elongated catheter, such as that shown at 141 in FIG. 3, is inserted through the working channel 165 for dispensing a somewhat viscous material into the surgical site, which in FIG. 8 comprises a vicinity of the lower esophageal sphincter 164. In the presently preferred embodiment, the elongate catheter 141 may have a length of, for example, about 1 meter to allow the elongate catheter to extend through the esophagus and to the lower esophageal sphincter 164.

The user presses the handle end 111 to thereby move the rod 113 distally against the syringe plunger 136. Distal movement of the plunger 136 forces viscous material within the syringe 140 distally out of the syringe 140 and through the elongate catheter 141. The elongate catheter 141 in the illustrated embodiment comprises a flexible material, such as a polymeric material, to facilitate maneuverability of the gastroscope 158. When the elongate catheter 141 is used in connection with a urethra procedure, such as the injection of bulking or filling material into a vicinity of a urinary sphincter, the elongate catheter 141 preferably comprises a surgical stainless steel. Injection procedures and apparatus, which utilize an elongate catheter and an accompanying syringe for treating, for example, urinary incontinence, and which are suitable for use with the injection facilitation apparatus 17 for urethral applications, are described in co-pending U.S. patent application Ser. No. 09/825,484, entitled URETHRA SURGICAL DEVICE, filed Apr. 2, 2001, the contents of which are expressly incorporated herein by reference.

A needle 173 is disposed at a distal end of the elongate catheter 141 for transferring viscous or other material from the elongate catheter 141 into tissue. The needle 173 penetrates into the tissue near the lower esophageal sphincter to inject a bulge 175 of bulking agent, as shown in FIG. 8. Additional bulking agent injections are formed around the lower esophageal sphincter 164 to thereby bulk up the tissue in the vicinity of the lower esophageal sphincter.

The needle preferably penetrates through the mucosa but not through the muscle layers of the lower esophageal sphincter 164, to thereby enable the injection of bulking material between these tissues. In modified embodiments, the needle may further be placed into the layers of muscle of the lower esophageal sphincter to facilitate the injection of bulking agent into these tissues as well. In urethral procedures, the needle preferably penetrates through the mucosa but not through the muscle layers of the urinary sphincter, to thereby facilitate the injection of bulking material between these tissues; and in modified embodiments, the needle is further inserted into the layers of muscle of the urinary sphincter to facilitate the injection of bulking agent into these tissues as well. Uses of the injection facilitation apparatus 17 are not limited to the above examples; the invention encompasses other foreseeable uses such as injections of viscous or other materials through elongate catheters into the colon, vagina, vessels, and other lumen structures.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. An injection apparatus, comprising:
   a transition-bore needle apparatus, which comprises a proximal end, a distal end, and a lumen extending from the proximal end to the distal end, wherein a diameter of the proximal end of the transition-bore needle apparatus is greater than a diameter of the distal end of the transition-bore needle apparatus, wherein a proximal portion of the transition-bore needle apparatus comprises a first needle having a first diameter, and a distal portion of the transition-bore needle apparatus comprises a second needle having a second diameter, and wherein the proximal end of the first needle defines a surface that is nonperpendicularly oriented to the lumen of the transition-bore needle apparatus.

2. The apparatus of claim 1, wherein the first needle is glued to the second needle.

3. The apparatus of claim 1, wherein the first diameter is greater than the second diameter.

4. The apparatus of claim 1, wherein the first needle comprises a proximal end, a distal end, and a first lumen extending through the first needle from the proximal end to the distal end, and wherein the second needle comprises a proximal end, a distal end, and a second lumen extending through the second needled from the proximal end of the second needle to the distal end of the second needle.

5. The apparatus of claim 1, wherein the transition-bore needle apparatus comprises a portion of the first lumen of the first needle and a portion of the second lumen of the second needle, and a juncture in the lumen of the transition-bore needle apparatus, where the diameter thereof transitions from the first diameter to the second diameter.

6. The apparatus of claim 5, wherein the proximal end of the first needle terminates within the second lumen, and where the termination is at the juncture of the transition-bore apparatus.

7. The apparatus of claim 1, wherein the proximal end of the first needle is beveled to improve flow of viscous material through the lumen of the transition-bore needle apparatus.

8. The apparatus of claim 1, wherein the proximal end of the first needle is chamfered to improve a flow of viscous material through the lumen of the transition-bore needle apparatus.

9. The apparatus of claim 1, wherein the proximal end of the first needle is beveled and chamfered to improve a flow of viscous material through the lumen of the transition-bore needle apparatus.

10. The apparatus of claim 1, further comprising a tissue stop disposed around a perimeter of the transition-bore needle apparatus.

11. The injection apparatus of claim 1, wherein the proximal end of the first needle defines an annular shoulder located in the second needle.

12. An injection apparatus, comprising a hand-held injection facilitation apparatus, which comprises:
    a body that retains a syringe;
    a rod disposed in the body, the rod comprising a distal end that contacts a proximal end of a syringe plunger; and
    a driving arm; and
    a pivot arm coupled to the rod and extending from the body so that movement of the pivot arm effects longitudinal displacement of the syringe plunger via the driving arm.

13. The injection apparatus of claim 12, wherein the body comprises a slot that accommodates a finger rest of the syringe.

14. The injection apparatus of claim 12, wherein the rod comprises a proximal end that has a spring disposed therearound, the spring being disposed between a proximal end of the body and an end of the pivot arm.

15. The injection apparatus of claim 12, wherein the pivot arm comprises an internal end disposed between two springs within the body, each of the springs providing opposing forces on the internal end of the pivot arm.

16. The injection apparatus of claim 12, wherein the rod has an end that extends from a proximal end of the body.

17. The injection apparatus of claim 12, further comprising a transition-bore needle apparatus coupled to the hand-held injection facilitation apparatus, wherein the transition-bore needle apparatus and the hand-held injection facilitation apparatus reduce the effort exerted by a person to eject a viscous material from the injection apparatus as compared to a syringe and catheter combination without a transition-bore needle apparatus and hand-held injection facilitation apparatus.

18. The injection apparatus of claim 12, wherein the driving arm is slidably coupled to the rod.

19. The injection apparatus of claim 12, wherein the pivot arm includes an internal end located in the body, the internal end of the pivot arm including a first internal end and a second internal end, and a handle end coupled to the second internal end and extending from the body, and wherein the driving arm is coupled to the rod at a position distal to the internal end of the pivot arm, the driving arm having a first end and a second end, the second end of the driving arm being located in proximity to the second internal end of the pivot arm; and the apparatus further comprises
    a pivot arm biasing assembly coupled to the internal end of the pivot arm and to the driving arm to bias the first internal end of the pivot arm and the first end of the driving arm in a first position when the pivot arm is in a relaxed position, wherein movement of the pivot arm handle towards the body causes the first internal end of the pivot arm to move proximally from the first position and causes the first end of the driving arm to move distally from the first position, movement of the internal end of the pivot arm and the driving arm from the first position being effective to distally displace the rod in the body.

20. The injection apparasus of claim 19, wherein the pivot arm biasing assembly comprises a handle spring disposed around a proximal portion of the rod, and being disposed between a proximal end of the body and the internal end of the pivot arm.

21. The injection appartus of claim 19, wherein the pivot arm biasing assembly comprises two springs located within the body and located on opposing sides of the internal end of the pivot arm, each of the springs providing opposing forces on the internal end of the pivot arm.

22. An injection apparatus for dispensing a viscous material, comprising
- a transition-bore needle apparatus, which comprises a needle at a distal end of the transition-bore needle apparatus, the needle having an outer diameter, end-a proximal and distal end, and a lumen extending from the proximal end to the distal end, the proximal end of the needle defining a surface that is nonperpendicularly oriented to the lumen of the needle; and at least one catheter having a distal end, the distal end of the at least one catheter sealingly attached to the proximal end of the needle so that fluid is displaced through a lumen of the catheter and the lumen of the needle without being displaced between the engagement of the catheter and the needle; and
- a hand-held injection facilitation apparatus coupled to the at least one catheter, the hand-held injection facilitation apparatus comprising a hollow body that retains a syringe that is attached to the catheter; a longitudinally displaceable rod disposed within the body, wherein a distal end of the rod contacts a proximal end of a syringe plunger; and a pivot arm coupled to the rod and extending from the body so that movement of the pivot arm causes longitudinal movement of the syringe plunger.

23. The injection apparatus of claim 22, further comprising a tissue stop disposed around the transition-bore needle apparatus so that the needle of the transition-bore needle apparatus is inserted a predetermined distance into a patient.

24. The injection apparatus of claim 22, further comprising a plurality of springs disposed on opposite sides of an internal end of the pivot arm to provide opposing forces to the internal end of the pivot arm.

25. The injection apparatus of claim 22, further comprising a slot within the body of the hand-held injection facilitation apparatus, the slot dimensioned to receive a finger rest of the syringe and to prevent distal displacement of the syringe from the hand-held injection facilitation apparatus.

26. The injection apparatus of claim 22, wherein the proximal end of the first needle defines an annular shoulder located in the second needle.

27. The injection apparatus of claim 22, wherein the hand-held injection appartus further comprises a driving arm, and movement of the pivot arm causes longitudinal movement of the syringe plunger via the driving arm.

28. The injection apparatus of claim 27, wherein the driving arm is slidably coupled to the rod.

29. The injection apparatus of claim 22, wherein the pivot arm includes an internal end located in the hollow body, the internal end of the pivot arm including a first internal end and a second internal end, and a handle end coupled to the second internal end and extending from the body; and wherein the handheld injection facilitation apparatus further includes
- a driving arm coupled to the rod at a position distal to the internal end of the pivot arm, the driving arm having a first end and a second end, the second end of the driving arm being located in proximity to the second internal end of the pivot arm; and
- a pivot arm biasing assembly coupled to the internal end of the pivot arm and to the driving arm to bias the second internal end of the pivot arm and the second end of the driving arm in a proximal position when the pivot arm is in a relaxed position, and to urge the second internal end of the pivot arm and the second end of the driving arm to a distal position when the pivot arm handle is directed toward the body, movement of the internal end of the pivot arm and the driving arm with respect to the rod being effective to distally displace the rod in the body.

* * * * *